US00PP19810P2

(12) United States Plant Patent
Klemm

(10) Patent No.: US PP19,810 P2
(45) Date of Patent: Mar. 10, 2009

(54) *PELARGONIUM* PLANT NAMED 'KLEPZO7200'

(50) Latin Name: *Pelargonium zonale*
Varietal Denomination: KLEPZ07200

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/077,269

(22) Filed: Mar. 18, 2008

(51) Int. Cl.
*A01H 5/00* (2006.01)

(52) U.S. Cl. ..... Plt./329

(58) Field of Classification Search ..... Plt./329
See application file for complete search history.

*Primary Examiner*—Annette H Para
(74) *Attorney, Agent, or Firm*—Jondle & Associates, P.C.

(57) ABSTRACT

A new *Pelargonium* plant particularly distinguished by a good compact growth habit that is ideal for pot plants, early flowering, dark green foliage, brilliant purple-red flower color, and good tolerance to weather conditions, is disclosed.

1 Drawing Sheet

Genus and species: *Pelargonium zonale.*
Variety denomination: 'KLEPZ07200'.

BACKGROUND OF THE NEW PLANT

The present invention comprises a new and distinct cultivar of *Pelagonium,* botanically known as *Pelargonium zonale,* and hereinafter referred to by the cultivar name 'KLEPZ07200'. The new cultivar originated from a hybridization made in July of 2003 in Stuttgart, Germany. The female parent was the *Pelargonium* plant 'KLEP01012' (U.S. Plant Pat. No. 13,743), while the male parent was the proprietary *Pelagonium* plant 'Z 21 222' (unpatented).

The new cultivar was first propagated in July 2004 in Stuttgart, Germany and has been asexually reproduced by vegetative cuttings in Stuttgart, Germany over seven generations. The present invention has been found to retain its distinctive characteristics through successive asexual propagations.

Plant Breeder's Rights for this cultivar were applied for in Switzerland on Jul. 6, 2007 and in Canada on Apr. 5, 2007. 'KLEPZ07200' has not been made publicly available more than one year prior to filing of this application.

SUMMARY OF THE INVENTION

The following are the most outstanding and distinguishing characteristics of this new cultivar when grown under normal horticultural practices in a greenhouse in Stuttgart, Germany.

1. Good compact growth habit that is ideal for pot plants;
2. Early flowering;
3. Dark green foliage;
4. Brilliant purple-red flower color; and
5. Good tolerance to weather conditions.

DESCRIPTION OF PHOTOGRAPH

This new *Pelargonium* plant is illustrated by the accompanying photograph which shows overall plant habit including blooms, buds, and foliage of the plant; the colors shown are as true as can be reasonably obtained by conventional photographic procedures. The photograph is of a plant about three months old, grown in a greenhouse (glasshouse) in Stuttgart, Germany, in January to April 2008.

DESCRIPTION OF THE NEW CULTIVAR

The following detailed descriptions set forth the distinctive characteristics of 'KLEPZ07200'. The data which defines these characteristics were collected from asexual reproductions carried out in Stuttgart, Germany. The plant history was taken on three month old plants which were planted as rooted cuttings in 12-cm pots in January to April 2008, and then grown in a greenhouse with covered glass. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Geraniacaea.
- *Species.*—*Pelargonium zonale.*
- *Common name.*—*Pelargonium (Geranium).*

Parents:
- *Female.*—Purple flowered *Pelargonium* plant 'KLEP0101' (U.S. Plant Pat. No. 13,743).
- *Male.*—Proprietary *Pelagonium* plant 'Z 21 222' (unpatented).

Plant:
- *Habit.*—Upright.
- *Height.*—22 cm to 26 cm.
- *Spread.*—22 cm to 24 cm.
- *Life cycle.*—Spring, summer to autumn.
- *Form.*—Rounded, bushy.
- *Time to produce a rooted cutting.*—18 to 20 days.
- *Time to bloom from propagation.*—Approximately 85 days.
- *Lastingness of inflorescence on the plant.*—12 to 22 days.

Stems:
- *Stem color.*—RHS 138A.

*Pubescence.*—Present.
*Stem form.*—Round.
*Diameter.*—0.6 cm to 1.5 cm.
*Length.*—Moderate.
*Internode length.*—0.8 cm to 1.2 cm.

Leaves:
*Arrangement.*—Alternate.
*Shape.*—Typical of geranium, kidney shaped.
*Apex.*—Round.
*Base.*—Open.
*Margin.*—Crenate.
*Surface* (*both surfaces*).—Dull.
*Length.*—5.0 cm.
*Width.*—8.0 cm.
*Color.*—Upper surface: RHS 137A. Lower surface: RHS 137D.
*Surface pubescence* (*both surfaces*).—Present, short.
*Petiole.*—Length: 6 cm. Color: RHS 138A.
*Venation pattern.*—Palmate.
*Venation color* (*both surfaces*).—RHS 137D.

Inflorescence:
*Flowering habit.*—Continuous.
*Umbels.*—Length: 10 cm. Diameter: 8 cm to 10 cm. Individual florets of the umbel: Depth: 1 cm to 2 cm. Diameter 4 cm.
*Flower buds.*—Cluster shape: Umbelliferous. Bud shape: Elliptical. Bud apex: Acute. Bud base: Truncate. Bud margin: Entire, smooth. Color: RHS 137D.
*Petals.*—Quantity per flower: 6 to 7. Shape: Rounded. Apex: Rounded. Base: Attenuate. Margin: Entire. Length: 2.4 cm. Width: 2.0 cm. Color: Upper lobes: RHS 74A. Lower lobes: RHS 74C.
*Fragrance.*—Absent.
*Sepals.*—Number per flower: 5. Shape: Elliptical. Apex: Acute. Base: Obtuse. Margin: Entire. Color (both surfaces): RHS 137C. Length: 0.8 cm to 1.0 cm. Width: 0.4 cm to 0.6 cm.
*Pedicel.*—Length: 2.5 cm. Diameter 0.15 cm. Color: RHS 137D and RHS 60B.
*Peduncle.*—Length: 12 cm to 16 cm. Diameter: 0.5 cm. Color: RHS 137D.

Reproductive organs:
*Stamens.*—Anther length: 0.3 cm. Filament length: 0.6 cm. Filament color: RHS 155D. Pollen amount: Moderate. Pollen color: RHS 33A.
*Pistils.*—Number: 1. Stigma color: RHS 74C. Style length: 0.5 cm. Style color: RHS 155C. Ovary arrangement: Club-shaped.

Fruit and seed set: No seed set observed. Disease and insect resistance: No particular resistance or susceptibility has been observed.

COMPARISON WITH PARENTAL AND COMMERCIAL CULTIVARS

'KLEPZ07200' differs from the female parent 'KLEP01012' (U.S. Plant Pat. No. 13,743) by having a red-purple flower color, while 'KLEP01012' has purple and light pink bi-colored flowers.

'KLEPZ07200' differs from the male parent 'Z 21 222' (unpatented), by having a compact growth habit, while 'Z 21 222' has a strong growth habit.

'KLEPZ07200' differs from the commercial cultivar 'Arcona 2000' (unpatented, also known as 'KLECONA' in U.S. application Ser. No. 09/250,015, now abandoned) by having a more compact growth habit and dark green leaves, while 'Arcona 2000' has a medium growth habit with medium-green leaves.

I claim:

1. A new and distinct cultivar of *Pelargonium* plant as shown and described herein.

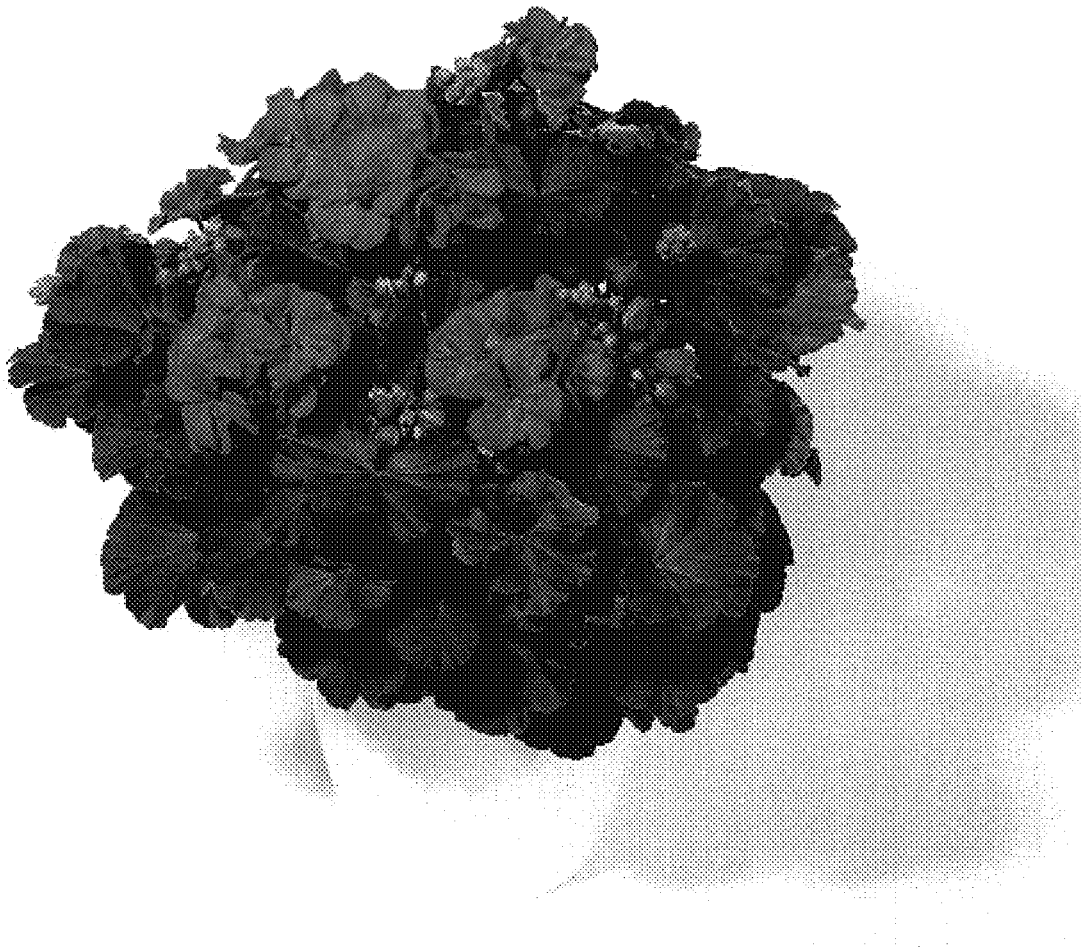

* * * * *